United States Patent
Schirmann

(10) Patent No.: US 6,517,798 B1
(45) Date of Patent: Feb. 11, 2003

(54) METHOD FOR PREPARING HYDRAZINE HYDRATE

(75) Inventor: Jean-Pierre Schirmann, Oullins (FR)

(73) Assignee: Atofino, Paris (FR)

( * ) Notice: Subject to any disclaimer, the term of this patent is extended or adjusted under 35 U.S.C. 154(b) by 0 days.

(21) Appl. No.: 09/674,580

(22) PCT Filed: May 6, 1999

(86) PCT No.: PCT/FR99/01073
§ 371 (c)(1),
(2), (4) Date: Oct. 31, 2000

(87) PCT Pub. No.: WO99/58445
PCT Pub. Date: Nov. 18, 1999

(30) Foreign Application Priority Data

May 14, 1998 (FR) .................................. 98 06078

(51) Int. Cl.$^7$ ...................... C01B 21/16; C07C 45/42
(52) U.S. Cl. ........................................ 423/407; 568/383
(58) Field of Search ........................... 423/407; 568/383

(56) References Cited

U.S. PATENT DOCUMENTS

| | | | |
|---|---|---|---|
| 3,494,737 A | * | 2/1970 | Mundil ........................ 423/407 |
| 4,725,421 A | * | 2/1988 | Schirmann et al. ......... 423/407 |
| 4,963,232 A | * | 10/1990 | Kuriyama et al. .......... 423/407 |
| 5,484,511 A | * | 1/1996 | Ohlendorf et al. .......... 423/407 |
| 5,744,115 A | * | 4/1998 | Kuriyama et al. .......... 423/407 |
| 5,986,134 A | * | 11/1999 | Kuriyama et al. .......... 423/407 |

* cited by examiner

Primary Examiner—Wayne A. Langel
(74) Attorney, Agent, or Firm—Pennie & Edmonds LLP

(57) ABSTRACT

The invention concerns a method for making hydrazine hydrate which consists in hydrolyzing methyl ethyl ketone azine to obtain hydrazine hydrate and methyl ethyl ketone, characterised in that it consists in purging heterocyclic compounds of the pyrazoline family to prevent coloration of the hydrazine hydrate.

7 Claims, 1 Drawing Sheet

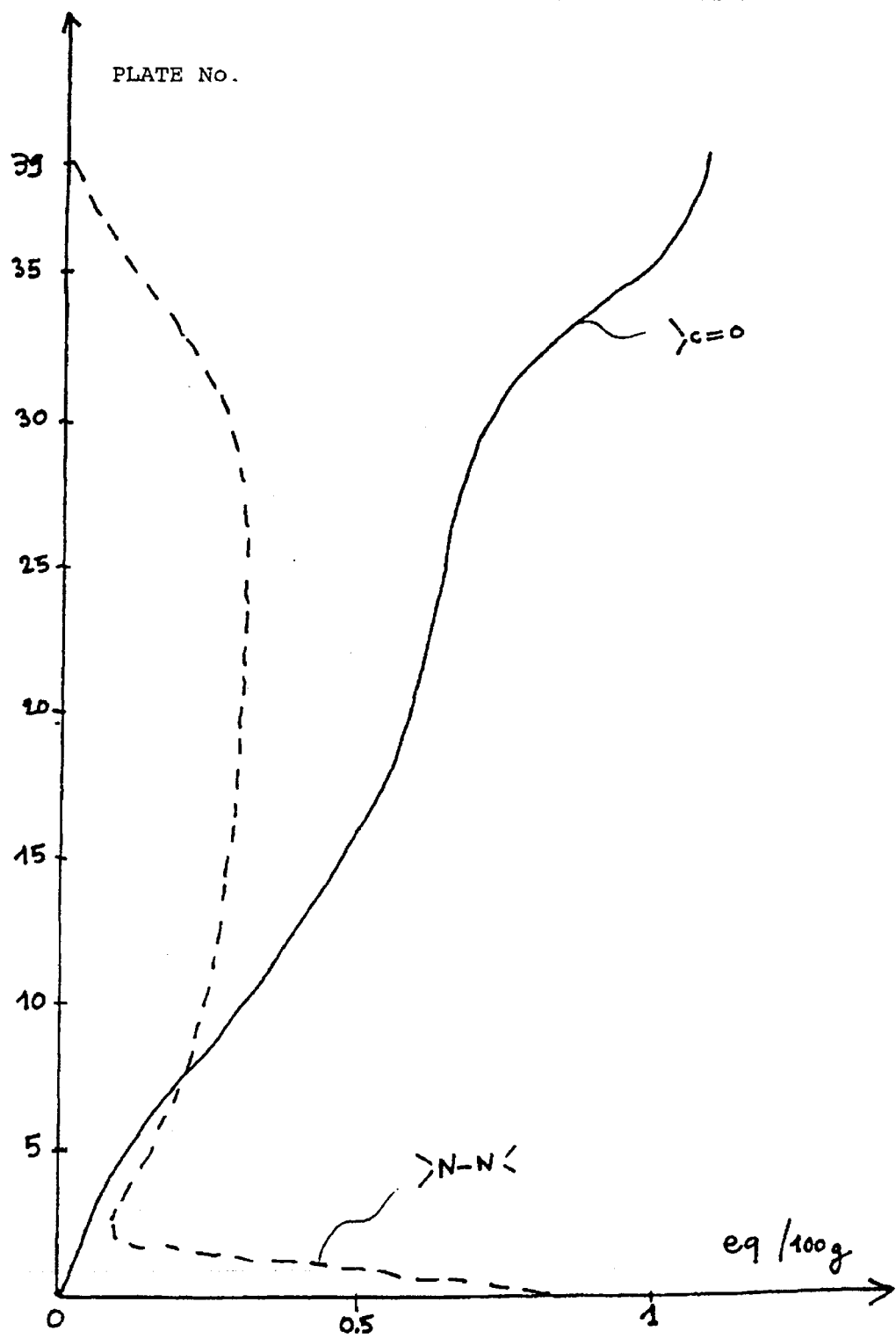
Fig. 1   PROFILE OF CONCENTRATIONS IN THE HYDROLYSIS COLUMN

METHOD FOR PREPARING HYDRAZINE HYDRATE

The present invention relates to a process for the preparation of hydrazine hydrate. The present invention relates more specifically to an improved process for the manufacture of hydrazine hydrate from methyl ethyl ketone azine.

The industrial production of hydrazine hydrate is carried out according to the Raschig, Bayer or hydrogen peroxide processes.

In the Raschig process, ammonia is oxidized with a hypochlorite in order to obtain a dilute hydrazine hydrate solution, which subsequently has to be concentrated by distillation. This process is not very selective, has a low yield and is highly polluting, and is virtually no longer used.

The Bayer process is an alternative form of the Raschig process which consists in shifting a chemical equilibrium by trapping, using a ketone, the hydrazine formed in the azine form. The azine is subsequently isolated and then hydrolysed to hydrazine hydrate. The yields are improved but there is no improvement with respect to the discharges to the environment.

The hydrogen peroxide process consists in oxidizing a mixture of ammonia and a ketone with hydrogen peroxide in the presence of a means for activating the hydrogen peroxide in order to directly form the azine, which it is sufficient subsequently to hydrolyse to hydrazine hydrate. The yields are high and the process is not polluting. The hydrogen peroxide process is used by the Applicant Company and is disclosed in numerous patents, for example U.S. Pat. No. 3,972,878, U.S. Pat. No. 3,972,876, U.S. Pat. No. 3,948,902 and U.S. Pat. No. 4,093,656.

The hydrolysis of an azine to hydrazine hydrate is disclosed in Patents U.S. Pat. No. 4,724,133 (Schirmann et al.), U.S. Pat. No. 4,725,421 (Schirmann et al.) and GB 1,164,460. This hydrolysis is carried out in a distillation column which is fed with water and azine. The ketone is recovered at the top and the hydrazine hydrate at the bottom.

EP 70,155 also discloses another hydrogen peroxide process.

These processes are also described in Ullmann's Encyclopaedia of Industrial Chemistry (1989), Vol. A 13, pages 182–183 and the references included.

In hydrogen peroxide processes, ammonia is oxidized with hydrogen peroxide in the presence of a ketone and of a means for activating the hydrogen peroxide according to the following overall reaction, an azine being formed:

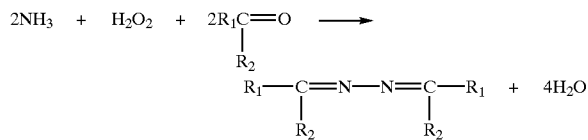

The activation means can be a nitrile, an amide, a carboxylic acid or a selenium, antimony or arsenic derivative. The azine is then hydrolysed to hydrazine and the regenerated ketone is recycled according to the following reaction:

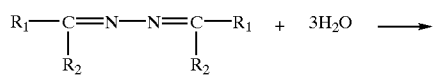

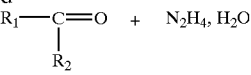

This hydrolysis is carried out in a distillation column. The ketone is recovered at the top and the hydrazine hydrate at the bottom.

Whether the azine originates from a hydrogen peroxide process or another method of preparation, this azine has to be hydrolysed in order to obtain the hydrazine hydrate. The present invention relates to the hydrolysis of methyl ethyl ketone azine (also known as mekazine in the continuation of the text), whatever its source, in order to convert it into hydrazine hydrate. The Applicant Company has discovered that heterocycles of the pyrazoline family were formed during hydrolysis and that, if the products are not bled off, the hydrazine hydrate is coloured.

The present invention relates to a process for the preparation of hydrazine hydrate in which methyl ethyl ketone azine is hydrolysed in order to obtain hydrazine hydrate and methyl ethyl ketone, characterized in that heterocycles of the pyrazoline family are bled off in an amount sufficient to prevent coloration of the hydrazine hydrate.

Whether the azine is produced by a hydrogen peroxide process or another process, methyl ethyl ketone is advantageously used because it has little solubility in the aqueous medium.

In the hydrogen peroxide process, methyl ethyl ketone azine was chosen industrially because it is relatively insoluble in the reaction mixture, which reaction mixture is necessarily aqueous since use is made of commercial aqueous hydrogen peroxide solutions assaying between 30 and 70% by weight. This azine is therefore easy to recover and to separate by simple settling. It is very stable, in particular in alkaline medium, that is to say in the ammoniacal reaction mixture. In all modern processes, this azine is subsequently purified and then hydrolysed in a reactive distillation column in order to release "at the end" methyl ethyl ketone at the top, to be recycled to the manufacturing reaction, and in particular an aqueous hydrazine hydrate solution at the bottom, which should comprise as few carbonaceous products as possible as impurities and should be colourless.

Although conventional packed columns can be suitable, use is generally made of plate columns. The number of plates can vary enormously according to the residence time allowed on the plates and the pressure, and therefore the temperatures at which the operation is carried out. In practice, when the operation is carried out under a pressure of 8 to 10 bar, the number of plates needed is of the order of 40 to 50.

This column is operated continuously and the reactants, that is to say mekazine and water, are injected into the top part of the column.

In point of fact, the Applicant Company has discovered that, when mekazine is hydrolysed according to the following equilibrium reactions:

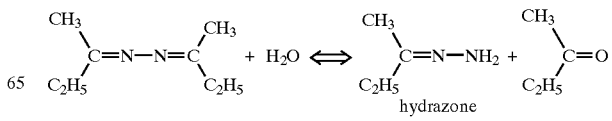

-continued

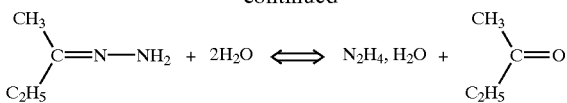

this end is clearly achieved, as indicated in FIG. 1, which represents the variations in

groups and in N—N groups along the entire length of the column. The amount of the groups is expressed in molar equivalent per 100 g of the sample under consideration. The carbonyl groups

are quantitatively determined by oximation, whereas the N—N groups are quantitatively determined by conventional iodometry after hydrolysis with sulphuric acid according to techniques known to a person skilled in the art. Plate 1 is at the bottom of the column and plate 40 is at the top. It is clearly observed that hydrolysis is complete, since the content of

groups in the bottom is zero, just as the content of N—N groups at the top is also zero.

However, the Applicant Company has also observed that, if care is not taken, although hydrolysis of the mekazine is complete, a hydrazine hydrate solution is obtained at the bottom which is not colourless but coloured and sometimes highly coloured, this being due to a content, sometimes a very high content, of carbonaceous products. In contrast to what might have been thought, these carbonaceous products are neither methyl ethyl ketone azine nor hydrazone but heterocycles derived from mekazine: 3,4,5-trimethyl-5-ethylpyrazoline

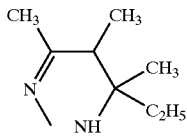

and 3,5-diethyl-5-methylpyrazoline

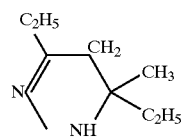

These compounds, which are isomers of mekazine, are formed in the hydrolysis column and are responsible for the yellow, indeed even brown or red, colorations which can be observed.

This hydrolysis is carried out, for example, in a plate or packed column of the distillation column type which is fed with the azine and water. The following are obtained: (i) at the top, methyl ethyl ketone with water, since an azeotrope with water is formed, and (ii) at the bottom, an aqueous hydrazine hydrate solution.

The hydrolysis of azines is known. For example, E. C. Gilbert, in an article in the Journal of the American Chemical Society, Vol. 51, pages 3397–3409 (1929), describes equilibrium reactions for the formation of azines and the hydrolysis reactions of the latter. The hydrolysis has to be carried out in a reactive column, such that, by continuously separating the methyl ethyl ketone at the distillation column top and the hydrazine hydrate at the column bottom, complete hydrolysis can be achieved. Of course, this system works best when the operation is carried out continuously, as disclosed in French Patent 1,315,348, British Patent 1,211, 547 or U.S. Pat. No. 4,725,421.

In all these patents, the reaction is carried out in a packed distillation column or better still a plate distillation column operating under a pressure of 2 to 25 bar with a bottom temperature of 150° C. to 200° C.

In this column, the azine is hydrolysed and the hydrazine hydrate is separated from the methyl ethyl ketone. These conditions are known. A person skilled in the art easily determines the number of plates or the packing height, as well as the points for feeding with azine and with water. Solutions comprising 30 or even up to 45% by weight of hydrazine hydrate are obtained at the bottom. This molar ratio of water to azine in feeding this column is at least greater than stoichiometry and advantageously between 5 and 7.75. The column bottom is between 150° C. and 200° C., preferably 175 to 190° C. The pressure depends on the boiling temperature of the azine, water and methyl ethyl ketone. Such a hydrolysis is disclosed in U.S. Pat. No. 4,725,721.

A person skilled in the art can easily determine, according to the number of plates or the packing height, the position of the azine feed and the position of the water feed, the reflux, the nature of the azine, and the like, in what part of the column the maximum concentration of 3,4,5-trimethyl-5-ethyl-pyrazoline and 3,5-diethyl-5-methylpyrazoline is obtained.

The Applicant Company has, moreover, just discovered that, while it is not possible to stop the formation of these by-products, it is at least possible to prevent these products from being found in the bottom of the column by taking a sidestream from a few plates. Sidestreams are advantageously taken from the plates with the maximum concentration of heterocycles of the pyrazoline family. The sidestream can be taken continuously but it is preferable to operate non-continuously, so as to avoid losing other products in the reaction process.

Amounts of the medium present in the hydrolysis column are drawn off such that the average concentration of these heterocycles in the concentration bulge does not exceed 4% and preferably 2% (by weight). The amount to be drawn off is easily determined by analysis, by gas chromatography, of the concentration of these heterocycles. These values are sufficient to prevent the hydrazine hydrate produced at the bottom from being coloured.

The present invention consequently relates to a process for the preparation of hydrazine hydrate, in which:
(a) ammonia, hydrogen peroxide and methyl ethyl ketone (MEK) are reacted in the presence of a working solution in order to form an azine;
(b) the working solution and the azine, optionally comprising unreacted methyl ethyl ketone, are separated;

(c) the working solution is recycled to the stage (a) after an optional treatment;

(d) the azine is hydrolysed in order to obtain hydrazine hydrate and to regenerate the methyl ethyl ketone;

(e) the methyl ethyl ketone is recycled to the stage (a), this process being characterized in that, in the stage (d), heterocycles of the pyrazoline family are bled off.

Stage (a)

The hydrogen peroxide can be used in the usual commercial form, for example as an aqueous solution comprising between 30 and 90% by weight of $H_2O_2$. One or more conventional stabilizers for peroxide solutions can advantageously be added, for example phosphoric acid, pyrophosphoric acid, citric acid, nitrilotriacetic acid or ethylenediaminetetraacetic acid or the ammonium or alkali metal salts of these acids. The amount to be used is advantageously between 10 and 1000 ppm and preferably between 50 and 250 ppm of the combined reactants and working solution at the reactor inlet. The ammonia can be anhydrous or in aqueous solution.

The working solution comprises a means for activating the hydrogen peroxide, that is to say a product such that azine can be produced from ammonia, hydrogen peroxide and methyl ethyl ketone.

This activator can be chosen from organic or inorganic oxyacids, their ammonium salts and generally their derivatives: anhydrides, esters, amides, nitrites, acyl peroxides, or their mixtures. Use is advantageously made of amides, ammonium salts and nitrites.

Mention may be made, by way of examples, of (i) amides of carboxylic acids of formula $R_5COOH$, in which $R_5$ is hydrogen, a linear alkyl radical having from 1 to 20 carbon atoms, a branched or cyclic alkyl radical having from 3 to 12 carbon atoms or a phenyl radical which can be substituted, or (ii) amides of polycarboxylic acids of formula $R_6(COOH)_n$, in which $R_6$ represents an alkylene radical having from 1 to 10 carbon atoms and n is an integer greater than or equal to 2, or $R_6$ can be a single bond and then n has the value 2. The $R_5$ and $R_6$ radicals can be substituted by halogens or OH, $NO_2$ or methoxy groups. Mention may also be made of the amides of the organic acids of arsenic. The organic acids of arsenic are, for example, methylarsonic acid, phenylarsonic acid and cacodylic acid.

The preferred amides are formamide, acetamide, monochloroacetamide and propionamide.

Use is advantageously made, among ammonium salts, of the salts of hydracids, of inorganic oxyacids, of arylsulphonic acids, of $R_5COOH$ acids or of $R_6(COOH)_n$ acids, $R_5$, $R_6$ and n being defined above, or of the organic acids of arsenic.

The preferred ammonium salts are the formate, acetate, monochloroacetate, propionate, phenylarsonate and cacodylate. Mention may advantageously be made, among the nitriles, of the products of formula $R_7(CN)_n$, it being possible for n to vary from 1 to 5, depending on the valency of $R_7$, and $R_7$ being a cyclic or non-cyclic alkyl having from 1 to 12 carbon atoms or benzene or pyridine. $R_7$ can be substituted by groups which are not oxidized in the reactor of the stage a, for example halogens or carboxyl, carboxylic ester, nitro, amine, hydroxyl or sulphonic acid groups.

The preferred nitriles are acetonitrile and propionitrile.

The working solution is formed by dissolving one or more products chosen from organic or inorganic oxyacids, their ammonium salts and generally their derivatives: anhydrides, esters, amides, nitriles, acyl peroxides, or their mixtures. Use is advantageously made of the preceding amides, ammonium salts or nitriles.

This solution can be aqueous or based on an alcohol or on a mixture of alcohol and water. Use is advantageously made, among the alcohols, of saturated aliphatic alcohols having from 1 to 6 carbon atoms and preferably 1 or 2 carbon atoms.

Use is also advantageously made of diols and more particularly of diols having from 2 to 5 carbon atoms. Mention may be made, for example, of glycol, propylene glycol, 1,3-propanediol, 1,3- and 1,4-butanediol and 1,5-pentanediol.

According to an advantageous form of the invention, the working solution is an alcoholic solution of an organic acid of arsenic and is disclosed in Patent EP 70,155, the contents of which are incorporated in the present application. According to another advantageous form of the invention, the working solution is an aqueous solution of an amide of a weak acid and of the ammonium salt corresponding to this acid, such as disclosed in Patent EP 487,160.

These amides of weak acids are derived from the corresponding carboxylic acids which have a dissociation constant of less than $5 \times 10^{-5}$, that is to say acids which have a pK of greater than 4.3 in aqueous solution at 25° C.

For the polycarboxylic acids, these are the acids for which the constant of the first ionization is less than $5 \times 10^{-5}$.

Mention may be made, by way of examples, of the carboxylic acids of formula $R_8COOH$, in which $R_8$ is a linear alkyl radical having from 1 to 20 carbon atoms, a branched or cyclic alkyl radical having from 3 to 12 carbon atoms or a phenyl radical which can be substituted, or of polycarboxylic acids of formula $R_9(COOH)_n$, in which $R_9$ represents an alkylene radical having from 1 to 10 carbon atoms and n is an integer greater than or equal to 2, or $R_9$ can be a single bond and then n has the value 2. The $R_8$ and $R_9$ radicals can be substituted by halogens or OH, $NO_2$ or methoxy groups. Use is preferably made of acetamide, propionamide, n-butyramide or isobutyramide.

The ammonium salt corresponding to acetamide is ammonium acetate.

It would not be departing from the scope of the invention to form the ammonium salt in situ, that is to say to use the corresponding carboxylic acid which gives the ammonium salt by reaction with ammonia.

The proportions of the amide and of the corresponding ammonium salt can vary within wide limits. Use is usually made of 1 to 25 parts of the ammonium salt per 5 parts of amide and preferably 2 to 10.

The reactants can be used in stoichiometric amounts. However, use is made, per mole of hydrogen peroxide, of 0.2 to 5 mol and preferably of 1.5 to 4 mol of methyl ethyl ketone and of 0.1 to 10 mol and preferably of 1.5 to 4 mol of ammonia. The amount of working solution is between 0.1 and 1 kg per mole of hydrogen peroxide. This amount depends on its quality, that is to say on its catalytic strength or its activity which makes it possible to convert the reactants to azine. The proportions of the reactants laid down above make it possible to obtain complete conversion of the hydrogen peroxide and a production of azine corresponding to more than 50%, and which can reach 90%, of the hydrogen peroxide charged.

The hydrogen peroxide, ammonia and MEK can be brought into contact with the working solution in any way.

The operation is advantageously carried out in a homogeneous medium or in a medium which provides at least sufficient solubilization of the reactants for it to be possible to obtain the azine. The reaction can be carried out in a very wide temperature range, for example between 0 and 100° C., and is advantageously carried out between 30 and 70° C. Although it is possible to carry out the reaction at any pressure, it is simpler to be at atmospheric pressure. However, the pressure can rise up to approximately 10 bar if this is necessary in order to preferably maintain the reaction of the stage a in the liquid phase.

The reactants can be introduced simultaneously or separately and in any order into the working solution. It is possible to use all kinds of reactors, stirred or nonstirred, or even simple tanks, which can be arranged in parallel or in series, cocurrentwise or countercurrentwise, or any combination of these possibilities.

Stage (b)

Known means, such as liquid-liquid extraction, distillation, separation by settling or any combination of these possibilities, are used to separate (i) the azine and optionally the excess MEK and (ii) the working solution.

The working solution can be treated in the stage (c).

The stages (a), (b) and (c) are disclosed, for example, in Patents EP 399,866 and EP 518,728, the contents of which are incorporated in the present application.

The stage (d) has been described above.

EXAMPLES

In a column made of 316 L stainless steel, with a height of 3 m and a diameter Ø=70 mm, which is equipped with 40 plates, each 80 mm apart, comprising a perforated single bell cap with a diameter of 27 mm [lacuna]. There are 14 holes in each bell cap, each with a diameter of 2 mm. The working volume of liquid retained on the plate is 33 ml. It can be adjusted by varying the height of the weir.

This column is equipped with temperature probes (thermocouples) on plates 3, 6, 10, 13, 15, 19, 26, 28, 31 and 37, as well as at the top and bottom. Side-stream outlets equipped with valves are installed at plates 3, 10, 19, 26, 31 and 37.

The reactants can be introduced at the level of plates 5, 8, 12, 19, 22, 26 and 34. The rate of reflux is measured using a precalibrated rotameter. The heat supply at the column bottom is provided by electrical heating. The shaft of the column is rendered adiabatic by a sheath of hot air obtained by electrical heating, so as to equilibrate the temperatures inside and outside the column.

The reactants are fed via metering pumps.

The condenser is fed with circulating hot oil maintained between 130 and 140° C.

The procedure used is as follows:

400 cm$^3$ of doubly deionized water are placed in the boiler, with a volume of 800 cm$^3$, of the column. After the entire apparatus has been sealed, heating is begun and the pressure is allowed to rise to 8 bar. Then, as the water rises up into the column, the inactive materials are bled off while maintaining the pressure at 8 bar. When the level of the boiler reaches 200 cm$^3$, the injection of water is begun at the 34th plate in order to continue to form the water ballast in the column at the rate of 645 g over 1 h 15 minutes. When the temperature reaches 162° C. at the 19th plate, the injection of azine is begun at the 26th plate at the rate of 543 g of 82.4% azine solution (3.2 mol) over 1 h 30 minutes. Bleeding of the inactive materials from the column is continued while maintaining the pressure at 8 bar. Reflux is allowed to begin and the apparatus is left at total reflux until the reflux liquid is homogeneous. The continuous introduction of the reactants is then begun, as well as drawing off at the bottom and top. The operation is carried out at reflux 1. The azine is introduced in the form of a mixture with MEK at the rate of 275.4 g/h (assaying 82.4% of azine) and of 289 g/h of doubly deionized water.

In view of what was said above regarding the conditions of formation of the pyrazoline in the column, it is absolutely essential at all cost to prevent azine from falling to the bottom. The shutdown procedure used consists in:

stopping the introduction of azine continuing the introduction of water continuing the distillation and the removal of MEK until the top temperature reaches 170° C., the boiling point of water at 8 bar.

The top temperature becomes established at 148° C., whereas the bottom temperature is 180–181° C. Under stationary conditions, 200 g/h of a colourless 35% hydrazine hydrate solution are drawn off from the bottom. The content of pyrazolines in plate 19 is 2.6% and 20 ml of a mixture of azine, MEK, pyrazolines and water are drawn off from this plate every 4 hours.

The MEK-water azeotrope is drawn off at the top, which azeotrope represents, after cooling, an organic phase of 300 g/h, assaying 86.5% of MEK, and an aqueous phase of 55 g/h, assaying 26% of MEK.

What is claimed is:

1. Process for the preparation of hydrazine hydrate in which methyl ethyl ketone azine is hydrolyzed in a column having a bottom and a top to obtain hydrazine hydrate at the bottom and methyl ethyl ketone at the top, wherein heterocycles of the pyrazoline family are bled off in an amount sufficient to prevent coloration of the hydrazine hydrate by taking a sidestream of the heterocycles from the hydrolysis column.

2. Process for the preparation of hydrazine hydrate, in which:

(a) ammonia, hydrogen peroxide and methyl ethyl ketone (MEK) are reacted in a working solution to form an azine;

(b) the working solution is separated from the azine, which optionally comprises unreacted methyl ethyl ketone;

(c) the working solution is recycled to the stage (a) after an optional treatment;

(d) the azine is hydrolyzed in a column having a bottom and a top to obtain hydrazine hydrate at the bottom and to regenerate the methyl ethyl ketone at the top, wherein heterocycles of the pyrazoline family are bled off by taking a sidestream of the heterocycles from the hydrolysis column;

(e) the methyl ethyl ketone is recycled to the stage (a).

3. Process according to claim 1 or 2, in which the heterocycles of the pyrazoline family are 3,4,5-trimethyl-5-ethylpyrazoline and 3,5-diethyl-5-methylpyrazoline.

4. The process of claim 1, wherein an average concentration of the heterocycles in the concentration bulge does not exceed 4% by weight.

5. The process of claim 4, wherein the average concentration of the heterocycles in the the concentration bulge does not exceed 2% by weight.

6. The process of claim 2, wherein an average concentration of the heterocycles in the concentration bulge does not exceed 4% by weight.

7. The process of claim 6, wherein the average concentration of the heterocycles in the the concentration bulge does not exceed 2% by weight.

* * * * *

UNITED STATES PATENT AND TRADEMARK OFFICE
CERTIFICATE OF CORRECTION

PATENT NO.   : 6,517,798 B1
DATED        : February 11, 2003
INVENTOR(S)  : Jean-Pierre Schirmann It is certified that error appears in the above-identified patent and that said Letters Patent is hereby corrected as shown below:

<u>Title page,</u>
Item [73], Assignee, should be spelled -- Atofina --

Signed and Sealed this

Sixteenth Day of September, 2003

JAMES E. ROGAN
*Director of the United States Patent and Trademark Office*

UNITED STATES PATENT AND TRADEMARK OFFICE
CERTIFICATE OF CORRECTION

PATENT NO.    : 6,517,798 B1
DATED         : February 11, 2003
INVENTOR(S)   : Jean-Pierre Schirmann It is certified that error appears in the above-identified patent and that said Letters Patent is hereby corrected as shown below:

<u>Title page,</u>
Item [73], Assignee, should be spelled -- ATOFINA --

This certificate supersedes Certificate of Correction issued September 16, 2003.

Signed and Sealed this

Eighteenth Day of November, 2003

JAMES E. ROGAN
*Director of the United States Patent and Trademark Office*